United States Patent [19]
Cherry

[11] Patent Number: 5,885,230
[45] Date of Patent: Mar. 23, 1999

[54] EXTERNAL GASTROESOPHAGEAL VALVE CLOSER

[76] Inventor: Veronica Cherry, 2525 S. Ocean Blvd., Highland Beach, Fla. 33487

[21] Appl. No.: 859,760

[22] Filed: May 21, 1997

[51] Int. Cl.[6] ....................................................... A61B 5/00
[52] U.S. Cl. ........................... 600/593; 600/595; 606/203
[58] Field of Search .................................. 600/587, 593, 600/595; 606/54, 57, 201–203

[56] References Cited

U.S. PATENT DOCUMENTS

| Re. 34,661 | 7/1994 | Grim | 602/27 |
|---|---|---|---|
| 606,465 | 6/1898 | Le Seur . | |
| 3,532,090 | 10/1970 | Ward | 128/121 |
| 3,578,773 | 5/1971 | Schultz | 128/78 |
| 3,637,207 | 1/1972 | Christensen | 600/595 |
| 4,022,197 | 5/1977 | Castiglia | 128/101 |
| 4,416,272 | 11/1983 | Nelkin | 128/96 |
| 4,787,379 | 11/1988 | Yeh | 128/95.1 |
| 4,807,640 | 2/1989 | Watson et al. | 600/595 |
| 4,846,462 | 7/1989 | Regnier et al. | 600/595 |
| 4,989,615 | 2/1991 | Hochberg | 600/587 |
| 5,088,478 | 2/1992 | Grim | 602/27 |
| 5,263,491 | 11/1993 | Thornton | 600/587 |
| 5,423,328 | 6/1995 | Gavish | 600/587 |

*Primary Examiner*—Max Hindenburg
*Attorney, Agent, or Firm*—Fish & Richardson P.C.

[57] ABSTRACT

A device and method relate to closing a user's gastroesophageal valve to prevent acid reflux from the user's stomach. The device includes a belt having an inner surface and at least one fastener, the belt being sized to fit around an upper abdominal area of the user. A pliable triangular insert contains a gel material, the insert being attachable to the inner surface of the belt and sized to fit over the triangular area between the ribs and directly below the breast bone of the user. The insert conforms to the shape of the user's body and imparts pressure to the upper abdominal area of the user over the user's lower esophagus and gastroesophageal valve when the belt is tightly fastened around the user.

11 Claims, 3 Drawing Sheets

EXTERNAL GASTROESOPHAGEAL VALVE CLOSER

BACKGROUND OF THE INVENTION

This invention relates to treating stomach acid reflux in a patient's esophagus, and in particular, maintaining the patient's gastroesophageal valve in a closed position with an external device that is worn by the patient.

When acid reflux from a patient's stomach enters the esophagus, the patient may experience painful symptoms due to the acid burning the lining of the esophagus. Internal medicinal treatments and surgery have been used to treat severe acid reflux. However, non-surgical external treatment of acid reflux avoids both the risks accompanying surgery and the introduction of medicine into the patient's stomach and esophagus.

SUMMARY OF THE INVENTION

In general, in one aspect, the invention features a device for closing a user's gastroesophageal valve to prevent acid reflux from the user's stomach. A belt has an inner surface and at least one fastener, the belt being sized to fit around an upper abdominal area of the user. A pliable triangular insert contains a gel material, the insert being attachable to the inner surface of the belt and sized to fit over the triangular area between the ribs and directly below the breast bone of the user, the insert further conforming to the shape of the user's body and imparting pressure to the upper abdominal area of the user over the user's lower esophagus and gastroesophageal valve when the belt is tightly fastened around the user.

Implementations of the invention may also include one or more of the following features. The gel may be a hydrated silicate gel.

A pocket may be attached to the inner surface of the belt for housing the insert. The pocket may be removably attached to the inner surface of the belt. The pocket may be removably attached by hook and loop fasteners.

The belt may be elastic and may be adjustable. The fastener may include hook and loop fasteners. The insert may be approximately 3 inches high, 3 inches wide at its widest point and 1½ inches thick.

In general, in another aspect, the invention features a method of closing a user's gastroesophageal valve to prevent acid reflux from the user's stomach. A pliable triangular insert containing a gel material is placed against an upper abdominal area of the user over the triangular area between the ribs and directly below the breast bone of the user. The insert is held in place with a belt sized to fit around the upper abdominal area of the user to conform the insert to the shape of the user's body and to impart pressure to the upper abdominal area of the user over the user's lower esophagus and gastroesophageal valve.

Implementations of the invention may also include the following feature. The belt may be tightened around the upper abdominal area of the user.

The invention has the advantage of treating stomach acid reflux externally without requiring surgery or medicinal treatment.

The invention has the further advantage of being a simple remedy for stomach acid reflux that is easy to apply.

Other features and advantage of the invention will become apparent from the following detailed description, and from the claims.

DESCRIPTION OF THE PREFERRED EMBODIMENTS

As shown in FIGS. 1–6, an external gastroesophageal valve closer 10 includes an insert 12 and a belt 14.

Figure 1:
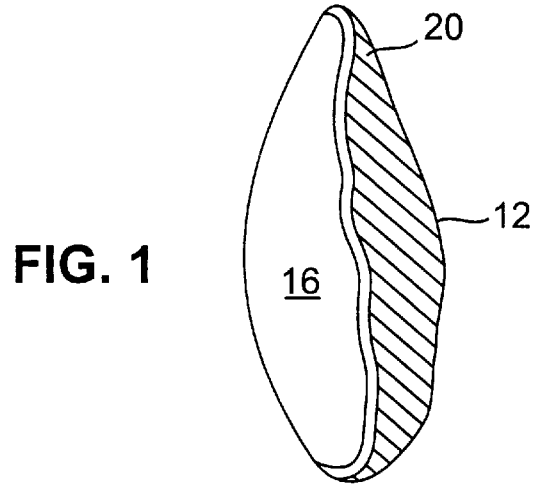
FIG. 1 is a side view of a triangular insert used with the external gastroesophageal valve closer of the present invention.
Figure 2:
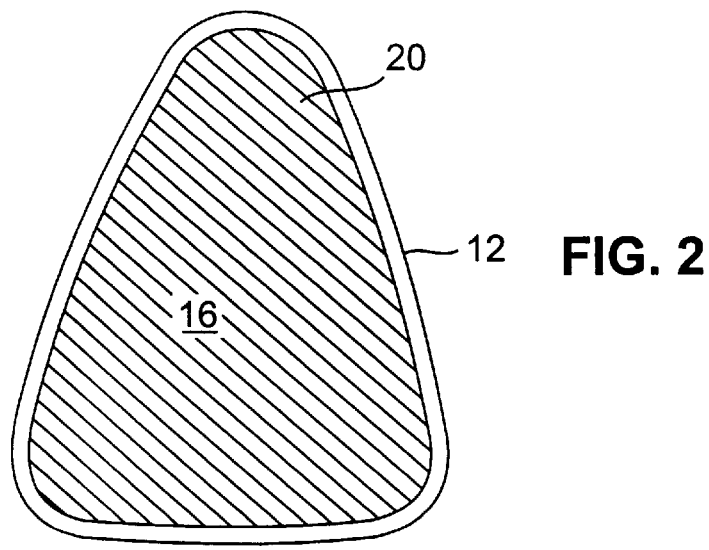
FIG. 2 is a front view of the triangular insert of FIG. 1.

Insert 12 has a triangular shape with an apex portion 20, as shown in FIGS. 1 and 2. Insert 12 may be constructed, e.g., from a pliable plastic material forming a sealed bag with front and back surfaces. Insert 12 is shaped to fit over the natural triangular space of a user's body formed between the ends of the user's left and right ribs directly beneath the breast bone in the user's upper abdominal area.

In a preferred embodiment, insert 12 is three inches in height, three inches wide at its widest point, and one and one half inches in thickness. Alternately, insert 12 may be custom-made to fit a particular user.

Insert 12 is filled with a gel material 16. Gel 16 may be, e.g., a hydrated silicate gel. Insert 12 is over-filled with gel 16 so that the front and back surfaces of insert 12 bulge to form approximately convex surfaces. Gel 16 permits insert 12 to mold to the contours of the user's body to prevent discomfort when insert 12 is placed against the user's upper abdominal area. The pliable plastic material and gel used to make the filled insert 12 may be any substances which have the properties described herein and which create an external gastroesophageal valve closer that is comfortably worn by the user.

Figure 4:
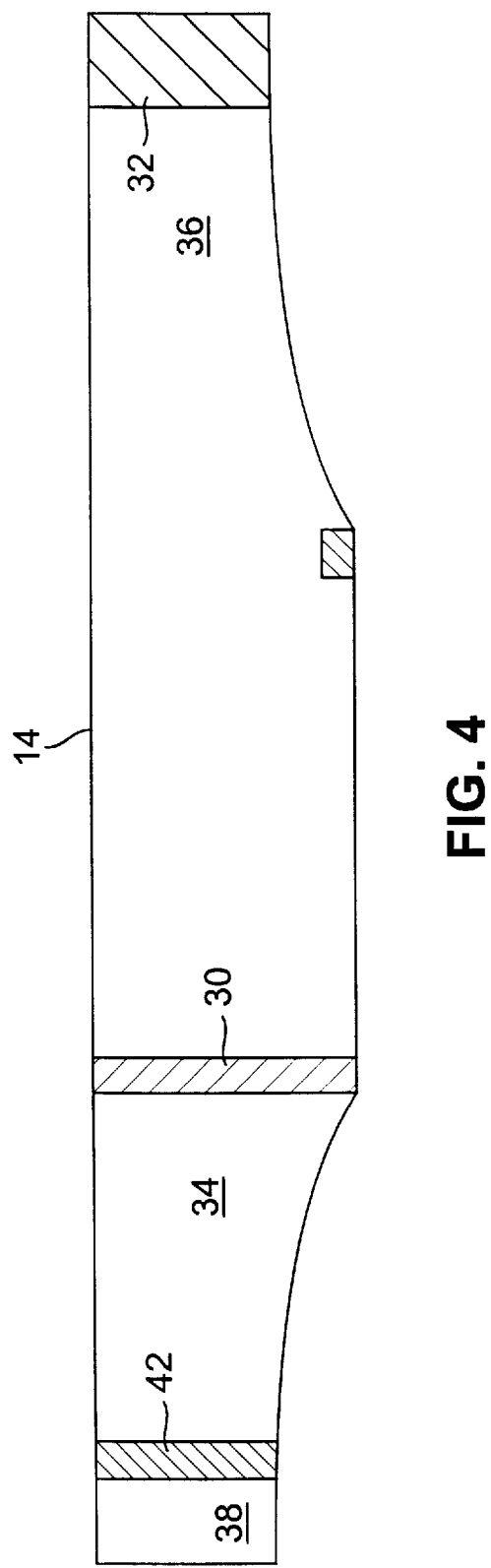
FIG. 4 shows a belt used with the external gastroesophageal valve closer of the present invention.

As shown in FIG. 4, belt 14 is made of a stretchable elastic material. Belt 14 is wrapped around the user's upper abdominal area and held in place, e.g., by corresponding strips of VELCRO™ hook and loop fasteners 30 and 32 on belt flaps 34 and 36. Belt 14 may be adjusted and tightened around the user's body by pulling flaps 34 and 36 tightly prior to placing strips 30 and 32 in contact with each other to mesh the VELCRO™ hook and loop fasteners.

Figure 3:
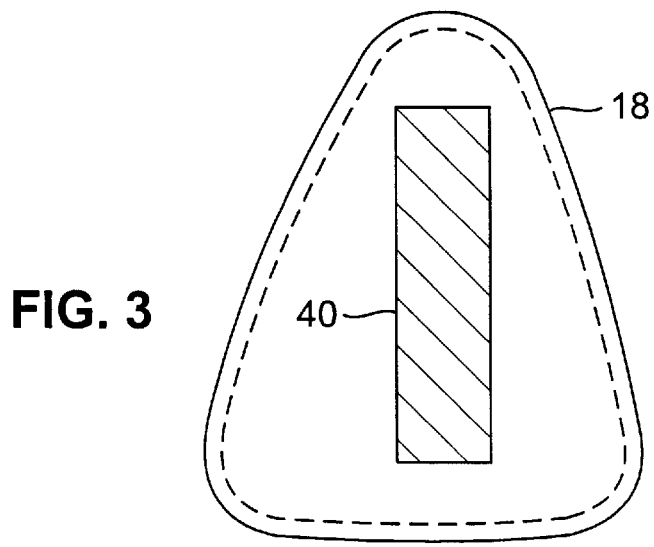
FIG. 3 shows a pocket into which the triangular insert of FIG. 1 may be placed.

Insert 12 is detachably connected to belt 14. As shown in FIGS. 3 and 4, insert 12 may be placed in a pocket 18 attachable to a front, inner surface 38 of belt 14. Pocket 18 may be made from two triangular pieces of fabric sewn together. Pocket 18 may open at the bottom for easy access to insert 12.

Pocket 18 may be attached to belt 14 by corresponding strips of VELCRO™ hook and loop fasteners. A first strip 40 may be fixed to pocket 18, and a second strip 42 may be attached to the front, inner surface 38 of belt 12 (FIG. 4). Since pocket 18 is removably attached to belt 14, and insert 12 may be removed from pocket 18, belt 14, pocket 18 and insert 12 may be disassembled so that pocket 18 and belt 14 may be cleaned without damaging insert 12.

Figure 5:
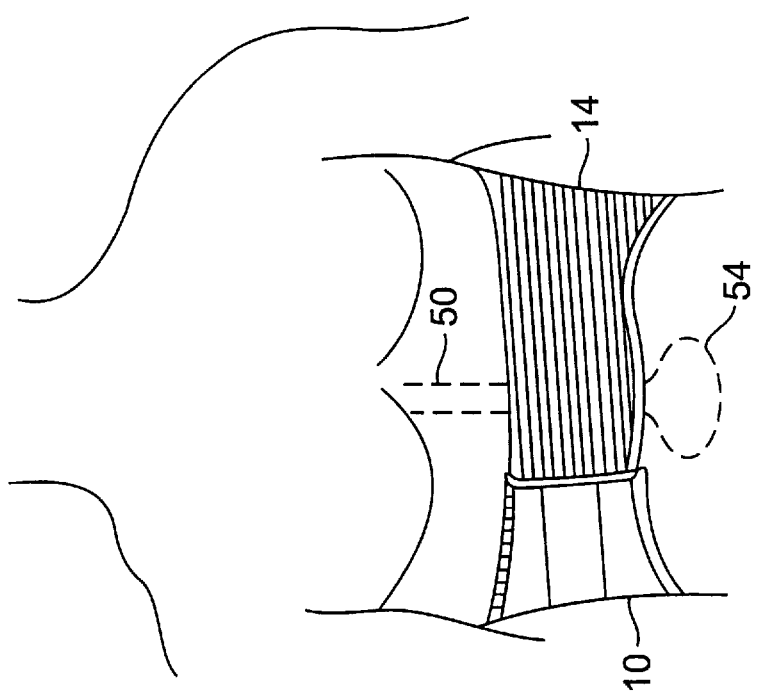
FIG. 5 shows the external gastroesophageal valve closer of the present invention placed on a user.
Figure 6:
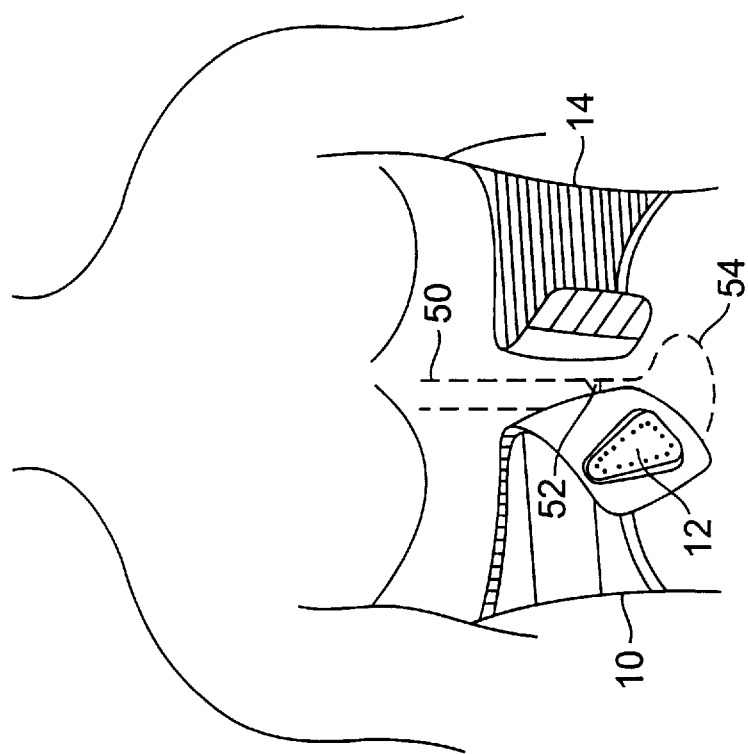
FIG. 6 shows the external gastroesophageal valve closer of FIG. 5 in an open position.

As shown in FIGS. 5 and 6, the assembled insert 12 and belt 14 are worn by a user around his or her upper abdominal area. Belt 14 is positioned on the user so that the apex portion 20 of insert 12 is placed immediately below the user's breast bone at the midline of the upper abdomen. Belt 14 is tightened so that insert 12 exerts pressure against the user's upper abdominal area. When belt 14 is placed around the user's upper abdominal area and tightened, a portion of gel 16 moves to the surface of insert 12 closest to the user's upper abdomen, thereby increasing its convexity and fitting into the contours of the user's body.

When belt 14 is tightened, insert 12 moves inwardly toward the user's lower esophagus 50. The user feels a firm pressure directed inward and downward with respect to his or her upper abdomen. Belt 14 should be comfortably positioned on the user without affecting the user's breathing and mobility.

Because insert 12 has a triangular shape with apex portion 20 facing upward, insert 12 has less surface area near apex portion 20. The inward pressure on insert 12 supplied by the tightened belt 14 causes apex portion 20 to move inward toward the user a greater distance than the bottom portion of insert 12, thus bending insert 12. This results in both inward and downward pressure against the user's lower esophagus 50. An increase in intra-abdominal pressure causes the user's esophagus 50 to bend inwardly. At the same time, increased intragastric pressure closes the gastroesophageal valve 52 over the user's stomach 54. The closure of the gastroesophageal valve 52 prevents reflux stomach acid from entering the user's esophagus 50.

Other embodiments are within the scope of the following claims.

What is claimed is:

1. A device for closing a user's gastroesophageal valve to prevent acid reflux from the user's stomach comprising:

a belt having an inner surface and at least one fastener, the belt being sized to fit around an upper abdominal area of the user; and a pliable triangular insert containing a gel material, the insert being attachable to the inner surface of the belt and sized to fit over the triangular area between the ribs and directly below the breast bone of the user, the insert further conforming to the shape of the user's body and imparting pressure to the upper abdominal area of the user over the user's lower esophagus and gastroesophageal valve when the belt is tightly fastened around the user.

2. The device according to claim 1 wherein the gel comprises a hydrated silicate gel.

3. The device according to claim 1 further comprising a pocket attached to the inner surface of the belt for housing the insert.

4. The device according to claim 3 wherein the pocket is removably attached to the inner surface of the belt.

5. The device according to claim 3 wherein the pocket is removably attached by hook and loop fasteners.

6. The device according to claim 1 wherein the belt is elastic.

7. The device according to claim 1 wherein the belt is adjustable.

8. The device according to claim 1 wherein the fastener comprises hook and loop fasteners.

9. The device according to claim 1 wherein the insert is approximately 3 inches high, 3 inches wide at its widest point and 1½ inches thick.

10. A method of closing a user's gastroesophageal valve to prevent acid reflux from the user's stomach comprising:

placing a pliable triangular insert containing a gel material against an upper abdominal area of the user over the triangular area between the ribs and directly below the breast bone of the user; and holding the insert in place with a belt sized to fit around the upper abdominal area of the user to conform the insert to the shape of the user's body and to impart pressure to the upper abdominal area of the user over the user's lower esophagus and gastroesophageal valve.

11. The method of claim 10 further comprising tightening the belt around the upper abdominal area of the user.

* * * * *